(12) United States Patent
Bullion-Lawarre

(10) Patent No.: US 12,717,163 B2
(45) Date of Patent: Aug. 25, 2026

(54) METAL DETECTABLE PROTECTIVE EYEWEAR

(71) Applicant: Radians, Inc., Memphis, TN (US)

(72) Inventor: Cynthia Bullion-Lawarre, Byhalia, MS (US)

(73) Assignee: RADIANS, INC., Memphis, TN (US)

( * ) Notice: Subject to any disclaimer, the term of this patent is extended or adjusted under 35 U.S.C. 154(b) by 306 days.

(21) Appl. No.: 18/432,708

(22) Filed: Feb. 5, 2024

(65) Prior Publication Data

US 2025/0248852 A1 Aug. 7, 2025

(51) Int. Cl.

| | |
|---|---|
| ***G02C 1/04*** | (2006.01) |
| ***A61B 90/00*** | (2016.01) |
| ***A61F 9/04*** | (2006.01) |
| ***G02C 5/18*** | (2006.01) |

(52) U.S. Cl.

CPC ................ *G02C 1/04* (2013.01); *A61B 90/39* (2016.02); *A61F 9/04* (2013.01); *G02C 5/18* (2013.01)

(58) Field of Classification Search

CPC ... G02C 1/04; G02C 5/14; G02C 5/18; G02C 5/186; G02C 5/2281

See application file for complete search history.

(56) References Cited

U.S. PATENT DOCUMENTS

| | | | | |
|---|---|---|---|---|
| 3,824,006 A * | 7/1974 | Voit | ......................... | G02C 1/04 351/178 |
| D495,729 S | 9/2004 | Hou | | |
| D502,725 S | 3/2005 | Yang | | |
| D544,018 S | 6/2007 | Huang | | |
| D547,356 S | 7/2007 | Yang | | |
| D547,357 S | 7/2007 | Yang | | |
| D548,768 S | 8/2007 | Yang | | |
| D633,553 S | 3/2011 | Cheng | | |
| D640,307 S | 6/2011 | Sheldon | | |
| D803,305 S | 11/2017 | Chou | | |
| D811,468 S | 2/2018 | Yang | | |
| D849,126 S | 5/2019 | Yang | | |
| 11,590,027 B2 | 2/2023 | San et al. | | |
| 11,690,762 B2 | 7/2023 | Love et al. | | |
| 2013/0271722 A1* | 10/2013 | DiChiara | ................. | G02C 7/02 351/140 |

(Continued)

FOREIGN PATENT DOCUMENTS

| | | | |
|---|---|---|---|
| CN | 104460028 A * 3/2015 | ............... | G02C 1/04 |
| CN | 113786280 A * 12/2021 | ............. | A61F 9/029 |

(Continued)

OTHER PUBLICATIONS

Machine translation of KR 20110010877 retrieved electronically from PE2E Search (Year: 2011).*

(Continued)

*Primary Examiner* — Cara E Rakowski

(74) *Attorney, Agent, or Firm* — Barnes & Thornburg LLP

(57) ABSTRACT

Protective eyewear includes a lens body, a metal marker, and a marker holder. The lens body has a first lens, a second lens, and a nosepiece interconnecting the first lens and the second lens. The marker holder is coupled to the lens body and formed to include a metal receiver to receive the metal marker therein so that the metal marker is detectable upon placement of the protective eyewear near a metal detector.

14 Claims, 14 Drawing Sheets

(56) References Cited

U.S. PATENT DOCUMENTS

| | | | | |
|---|---|---|---|---|
| 2017/0336652 | A1* | 11/2017 | Chen | G02C 5/00 |
| 2021/0069019 | A1* | 3/2021 | Love | A61F 9/02 |
| 2021/0353466 | A1 | 11/2021 | Love et al. | |
| 2023/0400711 | A1* | 12/2023 | Kocalar | G06F 1/163 |

FOREIGN PATENT DOCUMENTS

| | | | | | |
|---|---|---|---|---|---|
| CN | 113835236 | A | * | 12/2021 | G02C 5/14 |
| KR | 20110010877 | U | * | 11/2011 | G02C 11/02 |

OTHER PUBLICATIONS

Machine translation of CN 104460028 retrieved electronically from PE2E Search (Year: 2015).*

Machine translation of CN 113835236 retrieved electronically from PE2E Search (Year: 2021).*

Machine translation of CN 113786280 retrieved electronically from PE2E Search (Year: 2021).*

Advanced Detection Systems https://adsdetection.com/how-is-sensitivity-in-metal-detection-measured/ (Year: 2026).*

Office Action for U.S. Appl. No. 29/927,574, dated Jul. 16, 2025.

MetSafe MD1 IQ Metal-Detectable Wraparound Safety Glass, posted at indianasafety.com, posting date not given, [online], [site visited Jul. 14, 2025]. Available from Internet, URL: https://www.indianasafety.com/catalog/p/M D1-20-13/MetSafe-M D 1-IQ-Metal-Detectable-Wraparound-Safety-Glass-Blue-Clear-IQ/ (Year: 2025).

* cited by examiner 54
52
66
68
60
62
64
48

58
72
76
70
74
78
56
50

METAL DETECTABLE PROTECTIVE EYEWEAR

BACKGROUND

The present disclosure relates to protective eyewear, and particularly to protective eyewear that is metal detectable. More particularly, the present disclosure relates to protective eyewear having a metal marker that is metal detectable.

SUMMARY

Protective eyewear in accordance with the present disclosure includes temples, a lens body coupled to the temples, and a metal marker. The lens body includes a first lens, a second lens, and a nosepiece interconnecting the first lens and the second lens. In illustrative embodiments, the metal marker is metal detectable such that the protective eyewear is metal detectable upon placement near a metal detector.

In illustrative embodiments, the protective eyewear includes a marker holder coupled with a top portion of the lens body. The marker holder extends above the first lens, the nosepiece, and the second lens. The marker holder is shaped to define a marker receiver that receives the metal marker therein so that the metal marker extends above the first lens, the nosepiece, and the second lens.

In illustrative embodiments, the marker receiver is formed as an elongated, narrow groove that receives the metal marker therein so that the metal marker is not embedded into the lens body. The metal marker provides metal detectability to the protective eyewear.

BRIEF DESCRIPTIONS OF THE DRAWINGS

The detailed description particularly refers to the accompanying figures in which:

FIG. 1 is a front perspective view of protective eyewear in accordance with the present disclosure showing that the protective eyewear includes temples, a lens body coupled to the temples, and a marker holder coupled with the lens body and configured to receive a metal marker, and further showing that the marker holder is shaped to define a marker receiver formed as an elongated, narrow groove that receives the metal marker therein so that the metal marker is not embedded in the lens body and the protective eyewear is metal detectable;

FIG. 2 is an exploded assembly view of the protective eyewear of FIG. 1 showing that each of the temples is coupled to the lens body with a metal pin and the marker holder is coupled to a top portion of the lens body so that the marker holder and the metal marker received therein extend above a majority of the lens body, and further showing that the metal marker is a single component formed of elongated metal wire;

Figure 1:
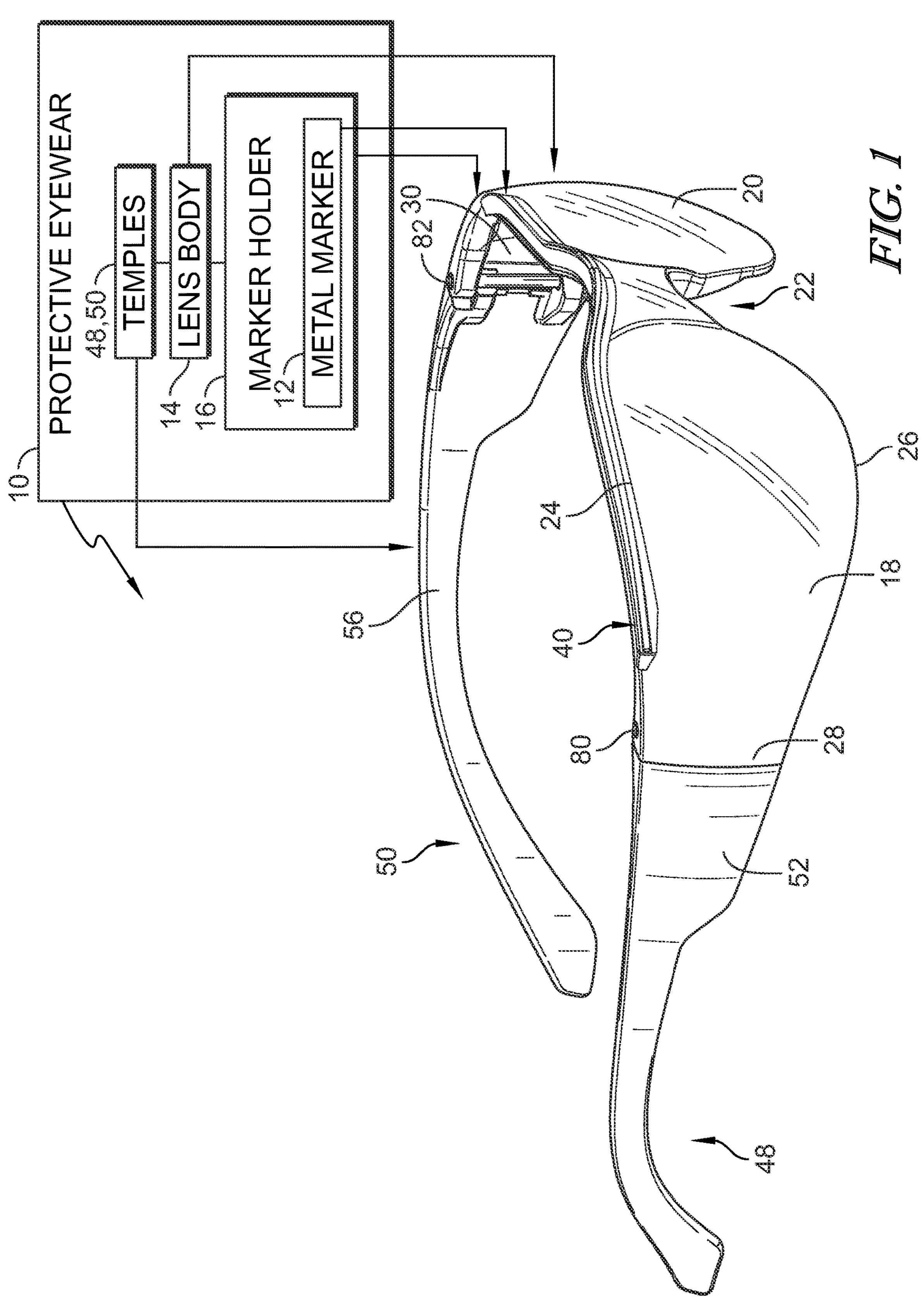
Figure 5:
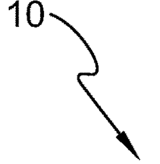
Figure 5:
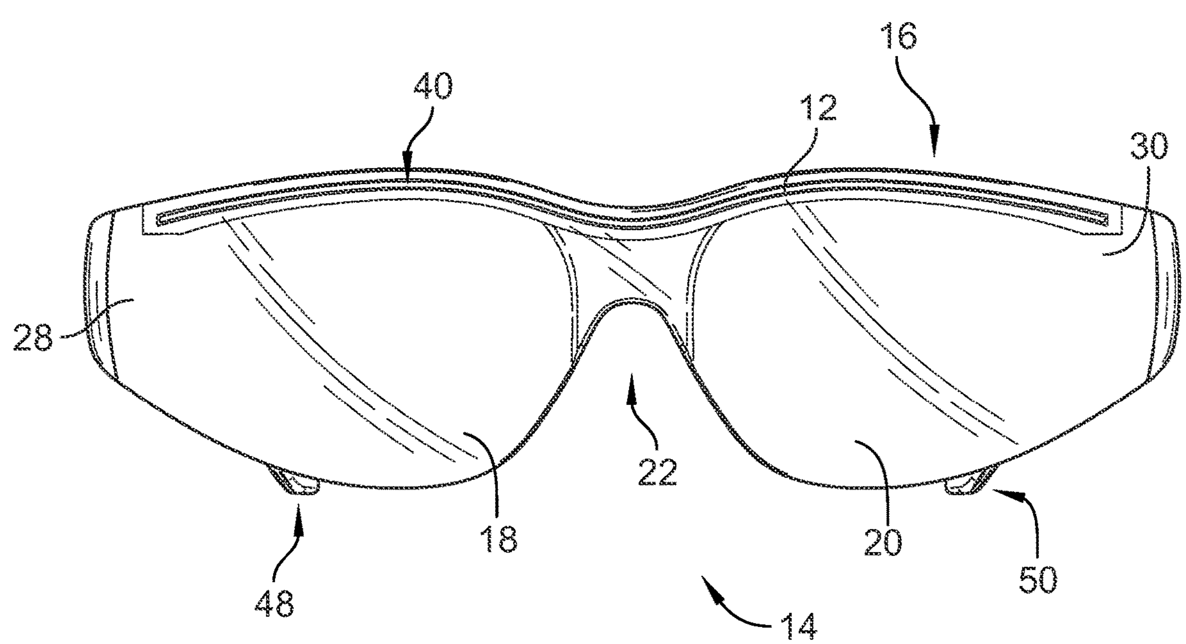
Figure 6:
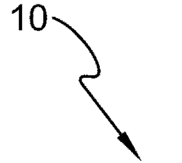
Figure 6:
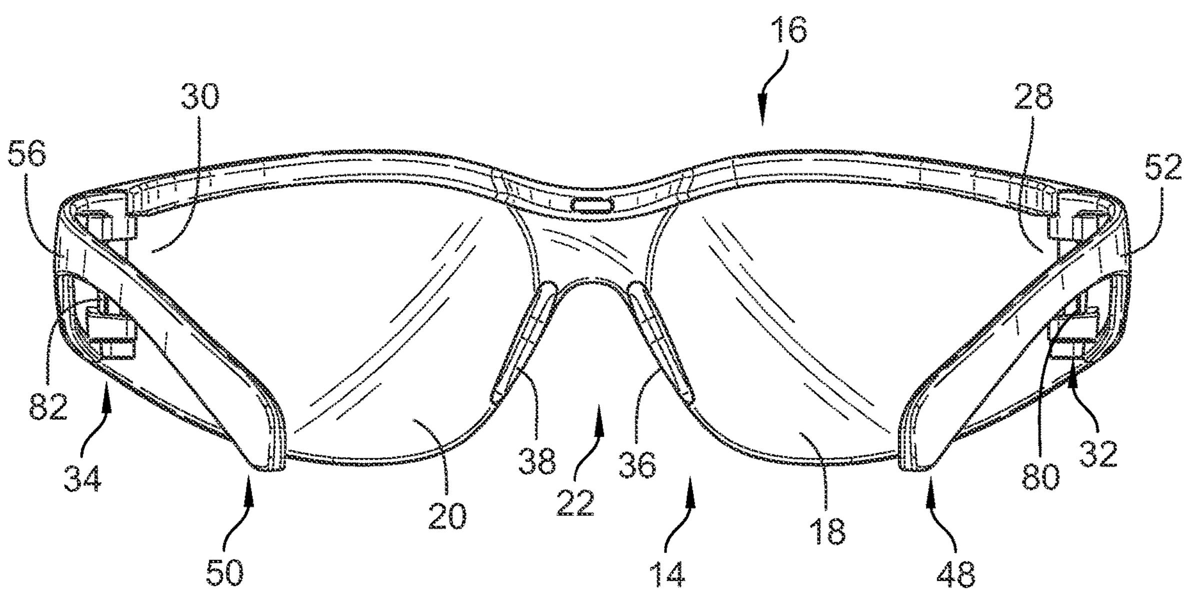
Figure 7:
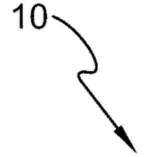
Figure 7:
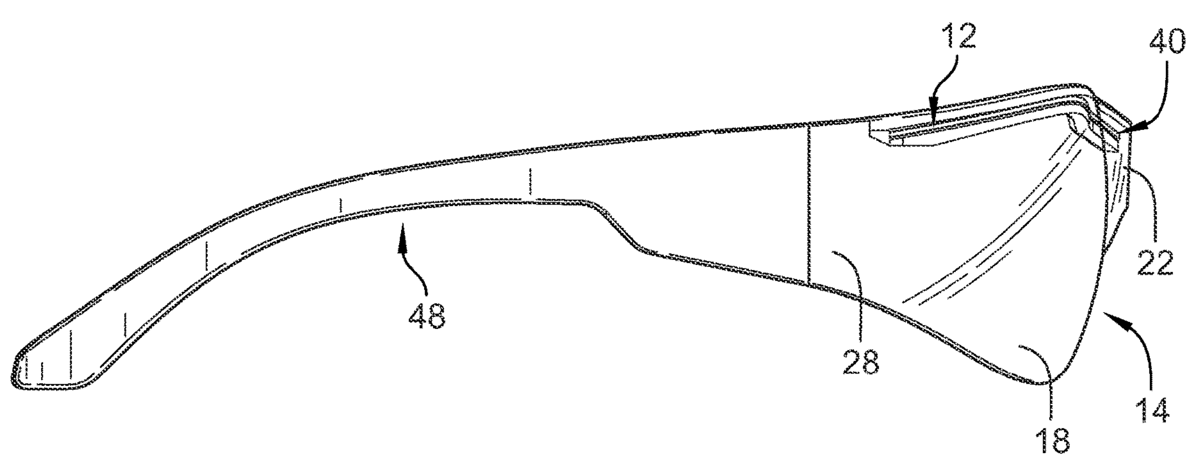
Figure 8:
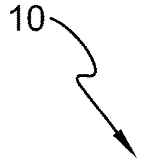
Figure 8:
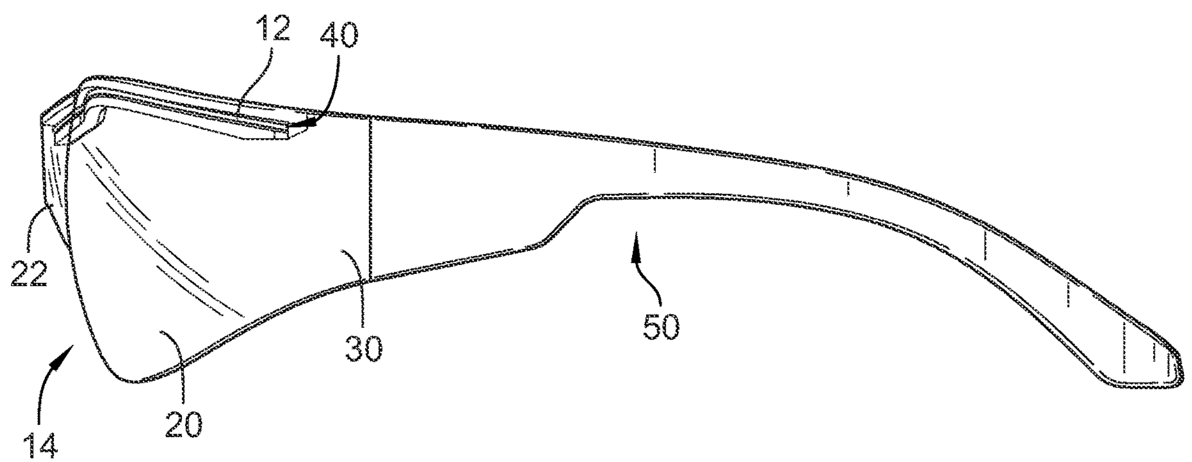
Figure 9:
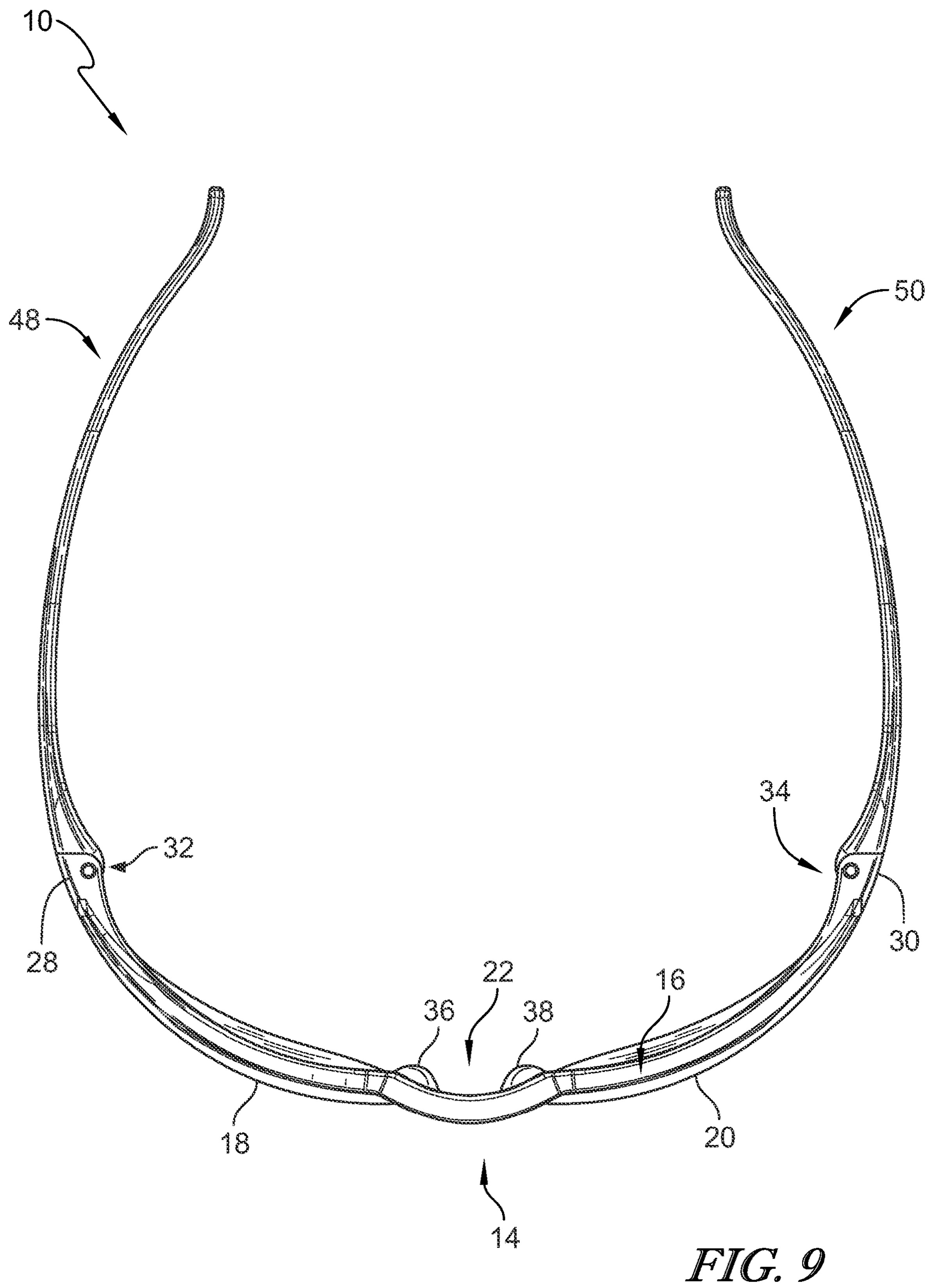
Figure 10:
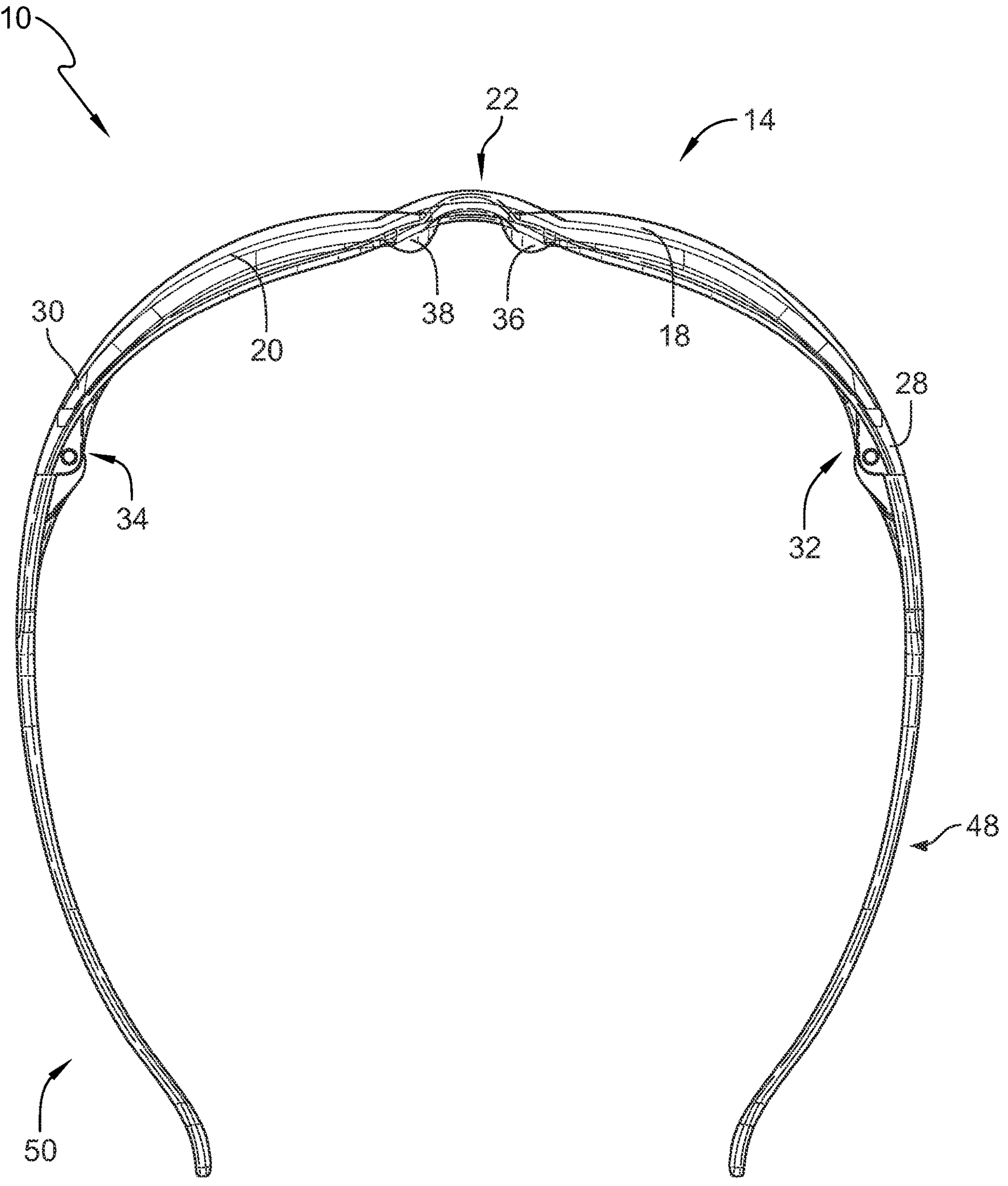
Figure 11:
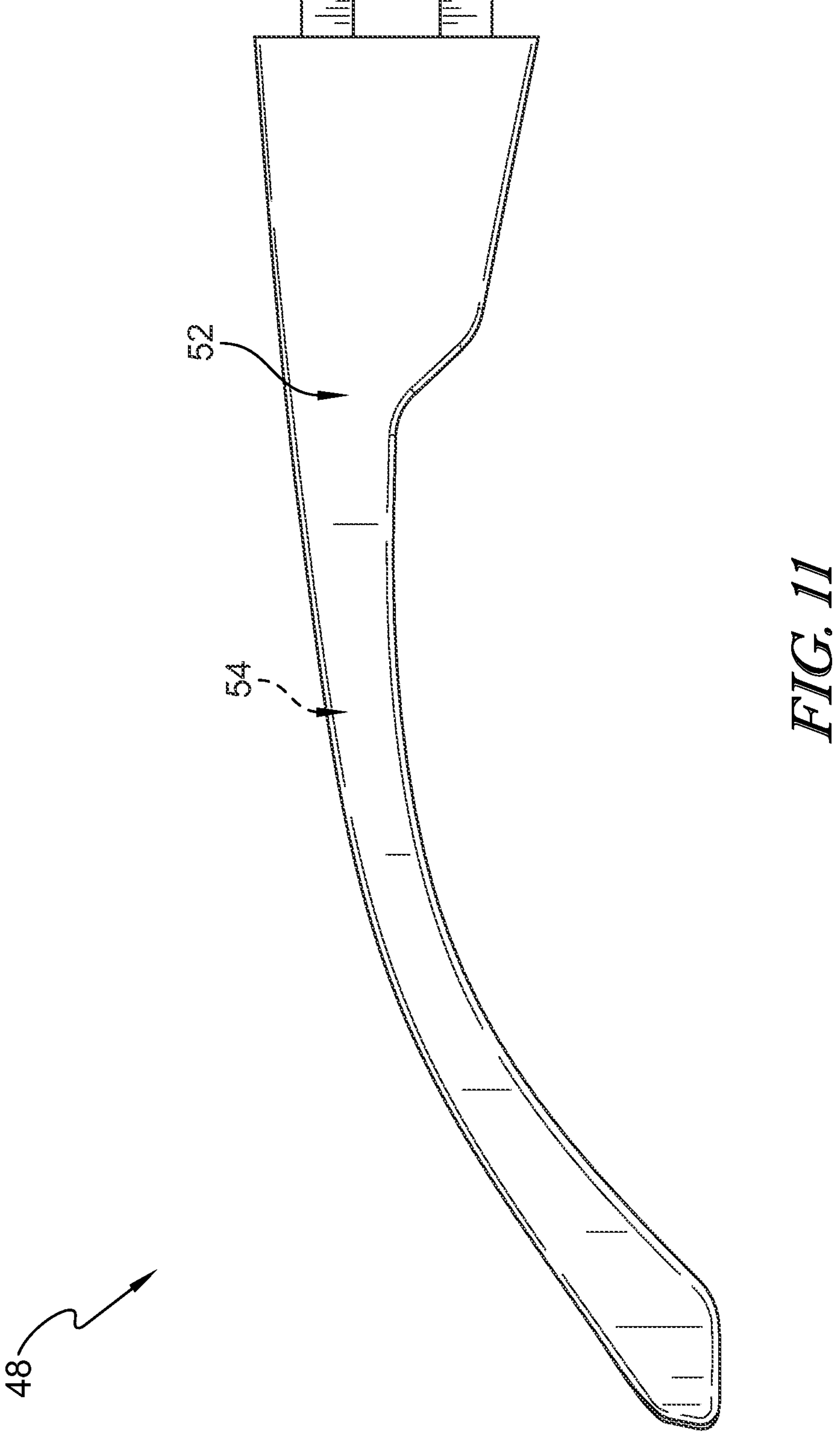
Figure 12:
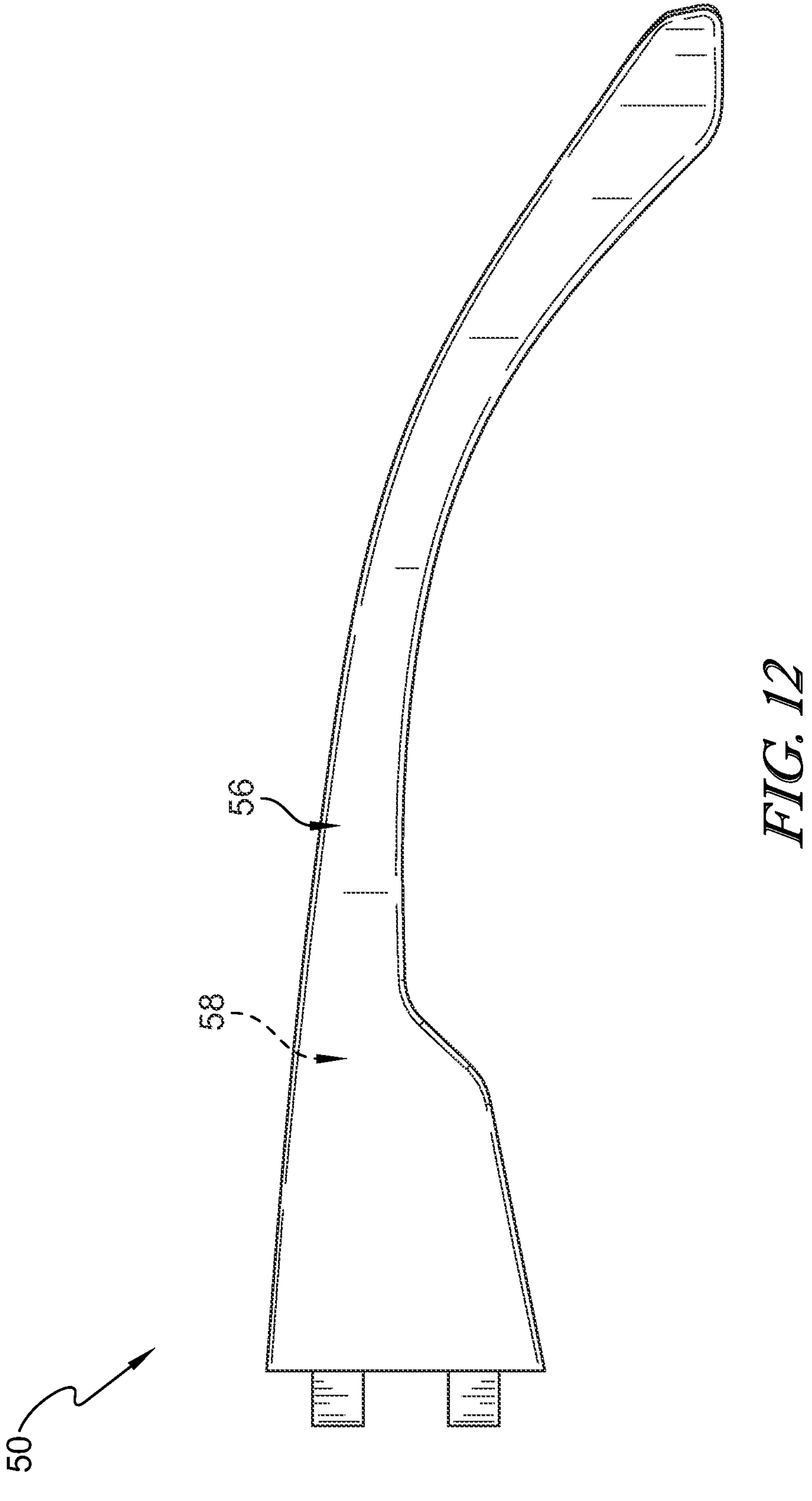
Figure 13:
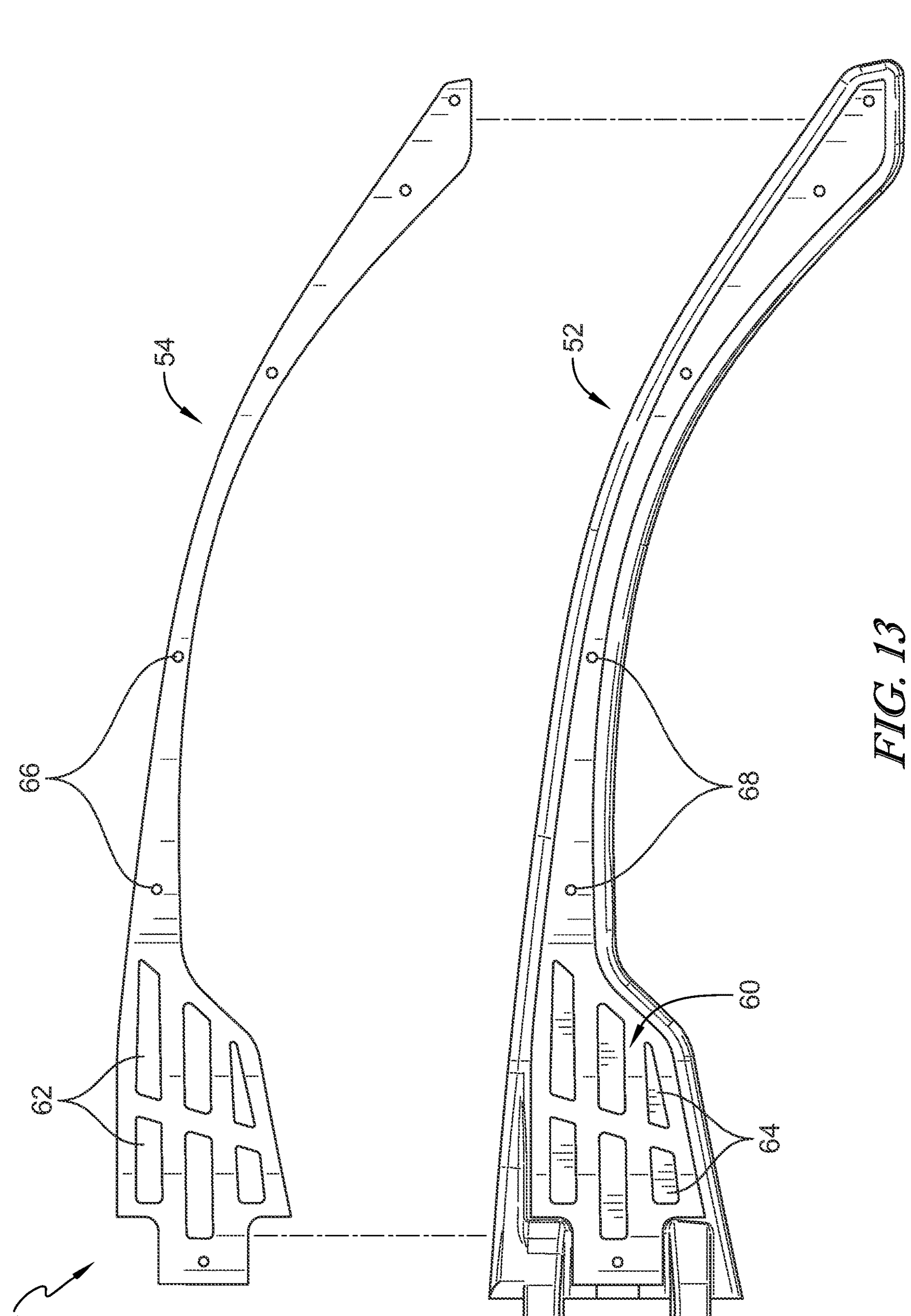
Figure 14:
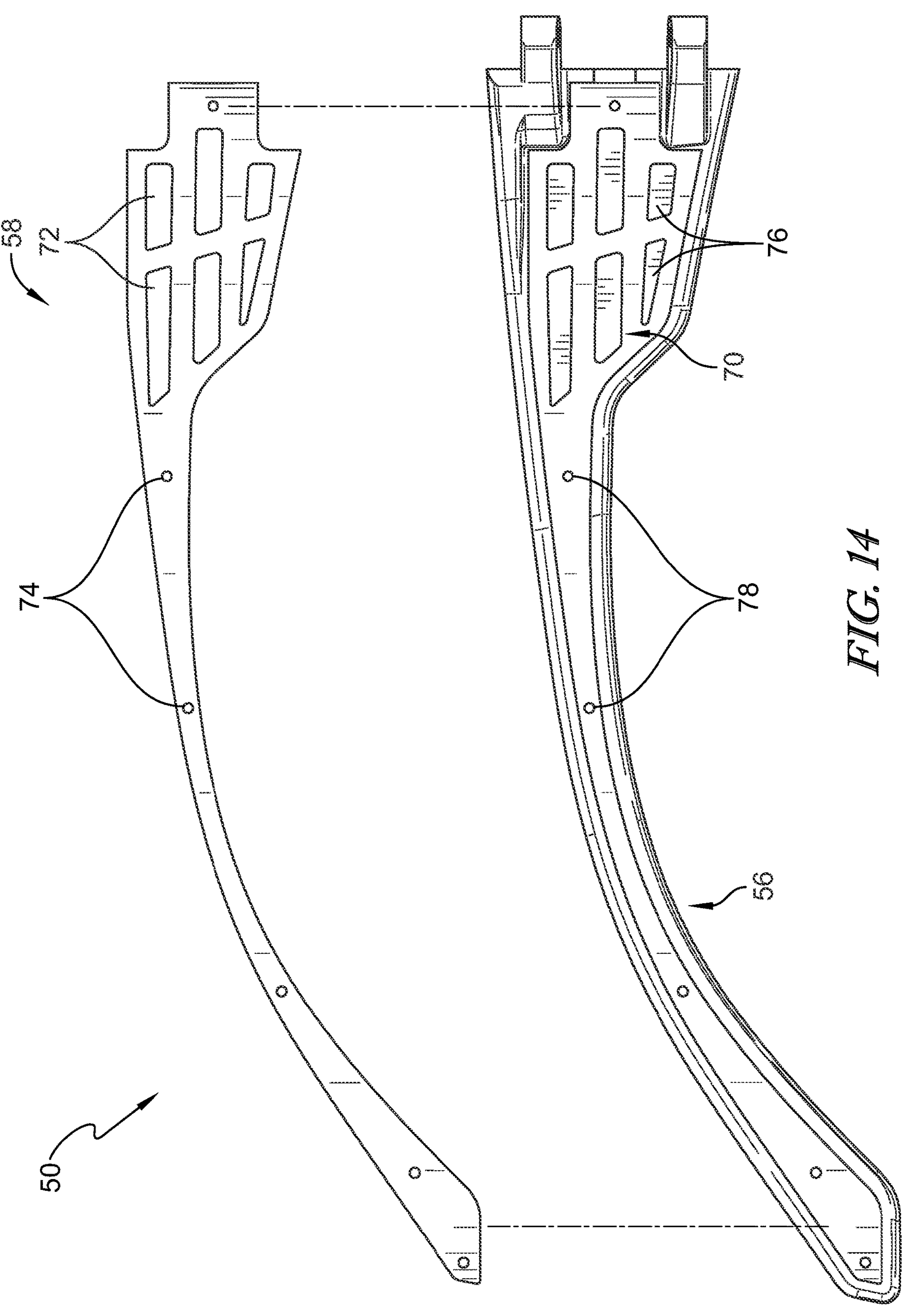

FIG. 5 is a front view of the protective eyewear of FIG. 1 showing that the lens body includes a first lens, a second lens, and a nosepiece interconnecting the first lens and the second lens, and further showing that the metal marker is positioned to lie in the forwardly-facing elongated, narrow groove of the marker holder so that the metal marker is visible from a front side of the protective eyewear;

FIG. 6 is a rear view of the protective eyewear of FIG. 1 showing that the metal marker positioned to lie in the forwardly-facing elongated, narrow groove of the marker holder is not visible from a rear side of the protective eyewear;

FIG. 7 is a side view of the protective eyewear of FIG. 1 showing that a first temple is coupled to the first lens by a first metal pin, and the first metal pin provides additional metal detectability to the protective eyewear;

FIG. 8 is an opposite side view of the protective eyewear of FIG. 1 showing that a second temple is coupled to the second lens by a second metal pin, and the second metal pin provides additional metal detectability to the protective eyewear;

FIG. 9 is a top view of the protective eyewear of FIG. 1 showing that the marker holder and the metal marker received therein extend above a majority of the lens body;

FIG. 10 is a bottom view of the protective eyewear of FIG. 1;

FIG. 11 is a perspective view of the first temple of the protective eyewear of FIG. 1;

FIG. 12 is a perspective view of the second temple of the protective eyewear of FIG. 1;

FIG. 13 is an exploded view of a portion of the first temple of the protective eyewear of FIG. 1 showing that the first temple includes a first temple body and a first metal plate arranged to lie within the first temple body to provide metal detectability to the first temple; and FIG. 14 is an exploded view of a portion of the second temple of the protective eyewear of FIG. 1 showing that the second temple includes a second temple body and a second metal plate arranged to lie within the second temple body to provide metal detectability to the second temple.

DETAILED DESCRIPTION

Figure 3:
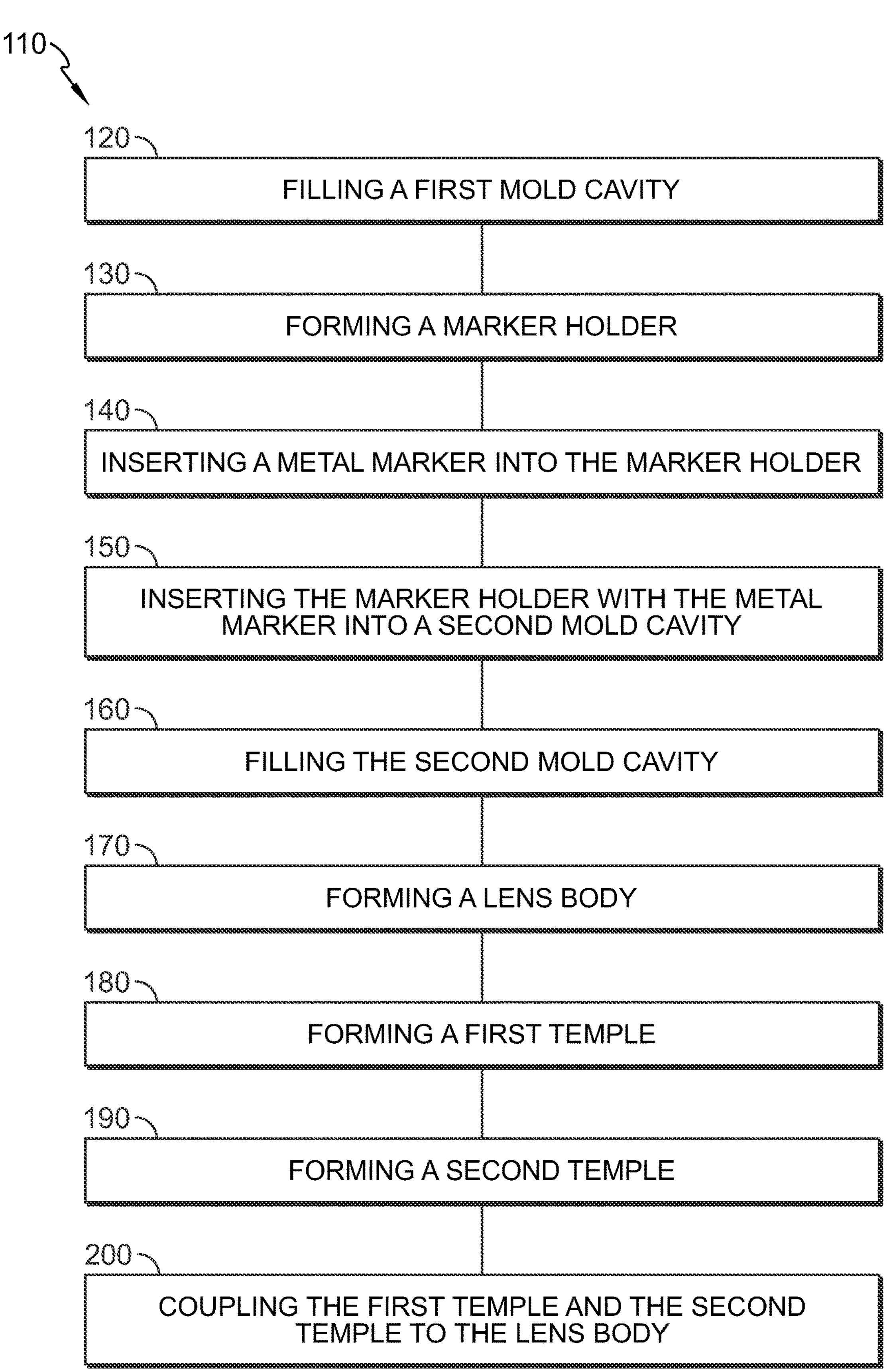
FIG. 3 is an illustration of a process of making the protective eyewear of FIG. 1.

Protective eyewear 10 in accordance with the present disclosure includes a metal marker 12, as shown in FIG. 1, so that the protective eyewear 10 is metal detectable. Protective eyewear 10 also includes a lens body 14 and a marker holder 16 that receives the metal marker 12 therein. The marker holder 16 is coupled with the lens body 14 in accordance with the present disclosure so that the metal marker 12 is not embedded in the lens body 14 as shown in FIG. 1. The marker holder 16 is formed to include a forwardly-facing metal receiver 40 to receive the metal marker 12 therein and to couple the metal marker 12 to the lens body 14 without inserting the metal marker 12 directly into the lens body 14. The metal marker 12 provides metal detectability to the protective eyewear 10 upon placement of the protective eyewear 10 near a metal detector. A process of making the protective eyewear 10 including the metal marker 12 is shown in FIG. 3.

Assembly line workers may wear protective eyewear, such as the protective eyewear 10, during food manufacturing, among other types of manufacturing. If the protective eyewear is broken, broken portions of the protective eyewear may pass undetected through machines intended to identify foreign objects. For example, packages of the food being manufactured may pass through machines to identify any foreign objects in the food. Thus, it is advantageous to provide metal detectable protective eyewear such that any broken portions of the protective eyewear may be detected as the packages of the food are passed through machines intended to identify foreign objects. The machines may include metal detectors, x-ray machines, or any other suitable machine for metal detection.

In addition to the advantageous metal detection quality of the protective eyewear 10, the optics of the protective eyewear 10 remain an important quality. Inserting metal, such as the metal marker 12, directly into a lens body may alter the optics of the lens body. For example, embedding metal in the lens body may cause the metal to torque on the lens body. The torqueing of the metal on the lens body may decrease visibility through the lens body by introducing distortion to the lens body. As such, in accordance with the present disclosure, the metal marker 12 is inserted into the marker holder 16, instead of directly into the lens body 14, to maintain the optics of the lens body 14.

The protective eyewear 10 comprises the metal marker 12, the lens body 14, and the marker holder 16 as shown in FIG. 1. The metal marker 12 comprises metallic material such that the metal marker 12 is metal detectable. The lens body 14 is configured to protect eyes of an eyewear user while the protective eyewear 10 is positioned on the eyewear user's head. The marker holder 16 retains the metal marker 12 therein and is coupled with the lens body 14 so as to couple the metal marker 12 to the lens body 14.

Figure 2:
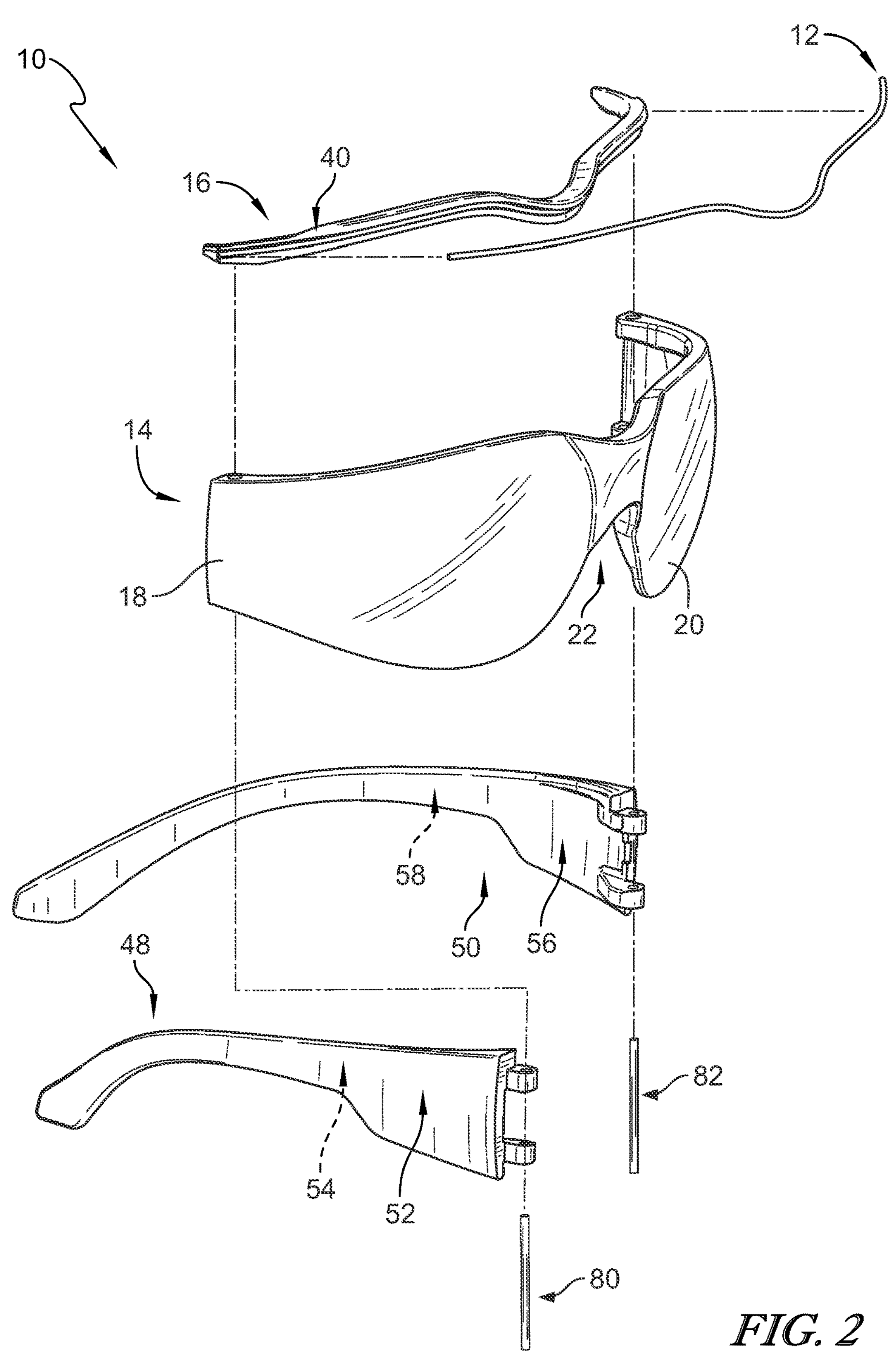
Figure 4:
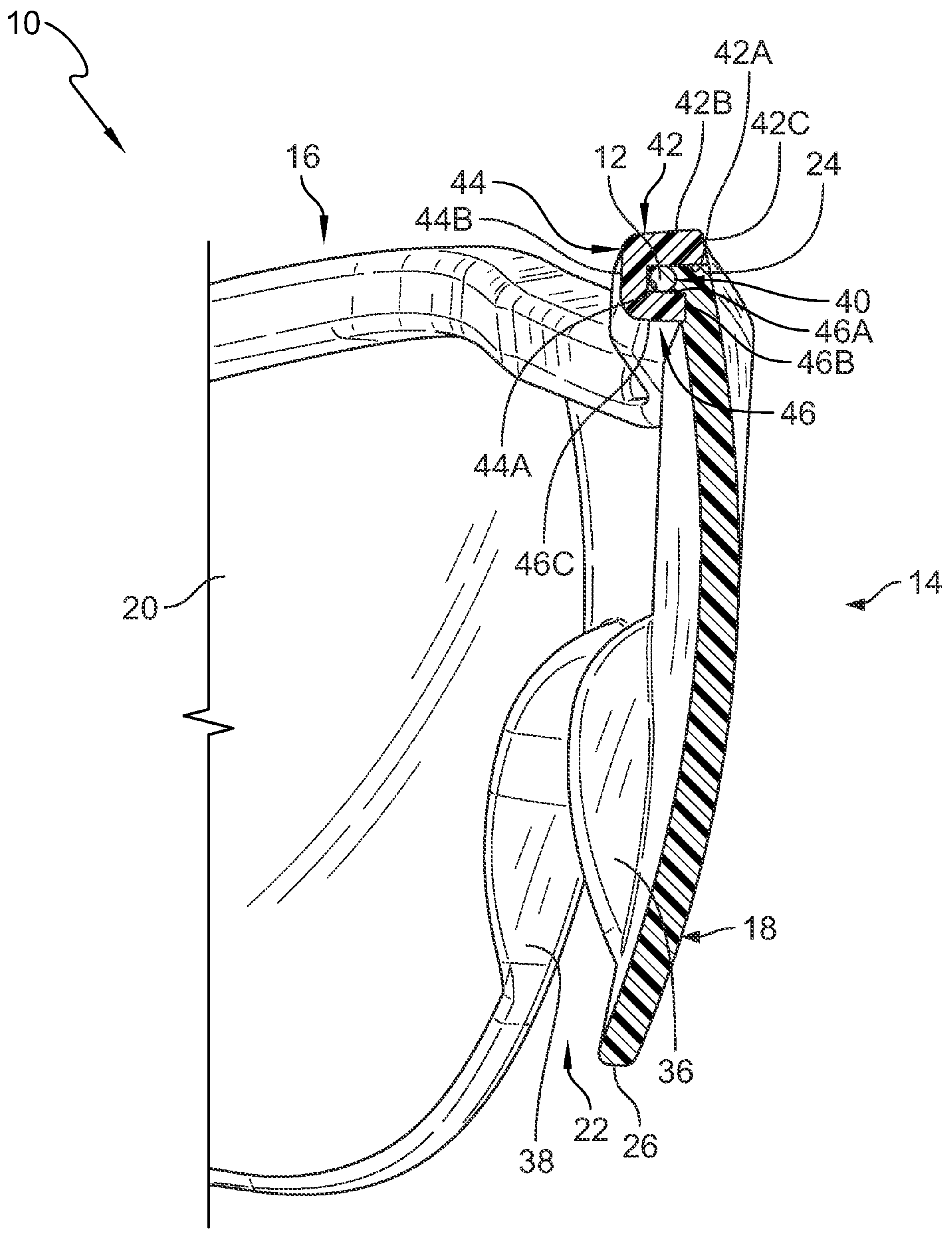
FIG. 4 is a cross-sectional view through the lens body of the protective eyewear of FIG. 1 showing that the marker receiver formed in the marker holder is a forwardly-facing elongated, narrow groove, and further showing that the lens body covers the forwardly-facing elongated, narrow groove of the marker receiver to fix the metal marker therein.

The metal marker 12 is illustratively formed as an elongated metal wire as shown in FIG. 2. In exemplary embodiments, the metal marker 12 is formed as a single, integral component. The metal marker 12 has a uniform cylindrical cross-sectional shape throughout an entirety of the metal marker 12 as shown in FIGS. 2 and 4. In some embodiments, the metal marker 12 includes only metallic material. The metallic material of the metal marker 12 may comprise stainless steel and/or any other suitable metallic material.

The lens body 14 includes a first lens 18, a second lens 20, and a nosepiece 22 as shown in FIGS. 1 and 5. The first lens 18 and the second lens 20 are arranged in front of respective eyes of the eyewear user such that the eyewear user looks through the first lens 18 and the second lens 20. The nosepiece 22 is disposed between the first lens 18 and the second lens 20 to interconnect the first lens 18 and the second lens 20. When in use, the nosepiece 22 rests on a nose of the eyewear user. The lens body 14 is formed to define a top portion 24 and a bottom portion 26 opposite the top portion 24 as shown in FIGS. 1 and 4. Each of the top portion 24 and the bottom portion 26 extend along the first lens 18, the nosepiece 22, and the second lens 20.

The lens body 14 is also formed to define a first side 28 and a second side 30 opposite the first side 28 as shown in FIGS. 5 and 6. The first side 28 interconnects the top portion 24 and the bottom portion 26, and the second side 30 interconnects the top portion 24 and the bottom portion 26. The first side 28 is formed on the first lens 18, and the second side 30 is formed on the second lens 20. The first side 28 defines a first hinge 32, and the second side 30 defines a second hinge 34 as shown in FIGS. 5 and 9.

The nosepiece 22 of the lens body 14 is formed to include a first nose pad 36 and a second nose pad 38 as shown in FIGS. 4 and 5. The first nose pad 36 and the second nose pad 38 are configured to rest on opposing sides of the nose of the eyewear user while the protective eyewear 10 is in use to support the protective eyewear 10 on the eyewear user's head.

Illustratively, the lens body 14 is formed as an integral component. The lens body 14 is made of an optically-transparent material such that the eyewear user can look through the first lens 18 and the second lens 20 of the lens body 14. The lens body 14 may be formed of polycarbonate or any other suitable optically-transparent material.

The lens body 14 is formed without a groove, a recess, a channel, or a metal receiver to receive the metal marker 12 therein. As shown in FIG. 1, the metal marker 12 is not inserted into a groove, a recess, a channel, or a metal receiver formed in the lens body 14. Instead, the marker holder 16 receives the metal marker 12 therein.

The marker holder 16 is formed to include the metal receiver 40 sized to receive the metal marker 12 therein as shown in FIGS. 1 and 4. The metal receiver 40 is a long, narrow groove that extends above the first lens 18, the second lens 20, and the nosepiece 22 as shown in FIG. 5. The metal receiver 40 is forwardly-facing such that the metal receiver 40 opens on a front side of the marker holder 16. While the protective eyewear 10 is in use, the metal receiver 40 opens away from the eyewear user.

The marker holder 16 includes a top wall 42, a back wall 44, and a bottom wall 46 as shown in FIG. 4. The top wall 42 and the bottom wall 46 lie in spaced-apart parallel relation to one another. The back wall 44 extends between and interconnects the top wall 42 and the bottom wall 46. The top wall 42, the back wall 44, and the bottom wall 46 cooperate to form the metal receiver 40. As shown in FIG. 4, a width of the top wall 42, as defined as a distance that the top wall 42 extends forwardly from the back wall 44, is greater than a width of the bottom wall 46, as defined as a distance that the bottom wall 46 extends forwardly from the back wall 44. The metal receiver 40 is open opposite the back wall 44 so that the metal marker 12 can be inserted the metal receiver 40. The metal marker 12 is arranged in the metal receiver 40 to engage a downwardly-facing surface 42A of the top wall 42, a forwardly-facing surface 44A of the back wall 44, and an upwardly-facing surface 46A of the bottom wall 46 as shown in FIG. 4. The metal receiver 40 allows the metal marker 12 to be included in the protective eyewear 10 without embedding the metal marker 12 directly in the lens body 14.

The marker holder 16 forms a topmost portion of the protective eyewear 10 as shown in FIG. 4. The marker holder 16 is coupled to the lens body 14 at the top portion 24 of the lens body 14 as shown in FIGS. 1 and 4. The top portion 24 of the lens body 14 extends into the metal receiver 40. The top portion 24 of the lens body 14 is illustratively formed as a rearwardly-extending lip. The top wall 42 of the marker holder 16 is arranged above the top portion 24 of the lens body 14 as shown in FIG. 4. The bottom wall 46 of the marker holder 16 is arranged below at least part of the top portion 24 of the lens body 14.

The lens body 14 mates and fuses with the downwardly-facing surface 42A of the top wall 42, the forwardly-facing surface 44A of the back wall 44, the upwardly-facing surface 46A of the bottom wall 46, and a forwardly-facing surface 46B of the bottom wall 46 as shown in FIG. 4. A downwardly-facing surface 46C of the bottom wall 46, a rearwardly-facing surface 44B of the back wall 44, an upwardly-facing surface 42B of the top wall 42, and/or a forwardly-facing surface 42C of the top wall 42 do not contact the lens body 14.

In some embodiments, the marker holder 16 may be formed from polycarbonate or any other suitable material. As suggested in FIGS. 5 and 6, in some embodiments, the materials of the marker holder 16 may be opaque. In some embodiments, the materials of the marker holder 16 are not transparent, such that the metal marker 12 is only visible through the open front side of the metal receiver 40. The materials of the marker holder 16 may comprise color pigment so that the materials of the marker holder 16 are opaque. In some embodiments, the materials of the marker holder 16 may be transparent. In some embodiments, the materials of the marker holder 16 may be translucent. In such an embodiment, the materials of the marker holder 16 may comprise color pigment so that the materials of the marker holder 16 are tinted.

The lens body 14 has a first top length that extends from the first side 28 to the second side 30 as shown in FIG. 5. The marker holder 16 has a second top length that is less than the first top length of the lens body 14 as shown in FIGS. 1, 5, and 7. Illustratively, the marker holder 16 does not extend entirely between the first side 28 and the second side 30 of the lens body 14. The metal receiver 40 formed in the marker holder 16 has a third top length that is less than the second top length of the marker holder 16. Illustratively, the metal receiver 40 is shorter than the marker holder 16 such that the metal receiver 40 does not have an opening on either distal ends of the marker holder 16. The metal marker 12 has a fourth top length that is less than the second top length of the marker holder 16. Thus, the metal marker 12 is arranged entirely between the two opposing ends of the marker holder 16.

To form the marker holder 16, a first mold cavity is filled with liquid materials. The first mold cavity forms the marker holder 16 with the metal receiver 40 as shown in FIG. 2. The marker holder 16 is illustratively formed through injection molding. The metal marker 12 is bent to match a shape of the metal receiver 40 as suggested in FIG. 2. The metal marker 12 is inserted into the metal receiver 40 through the opening on the front side of the marker holder 16. In some embodiments, the metal marker 12 is manually inserted into the metal receiver 40 by a technician. The marker holder 16 with the metal marker 12 arranged therein is positioned in a second mold cavity. In some embodiments, the marker holder 16 with the metal marker 12 is manually inserted into the second mold cavity by a technician. The lens body 14 is molded over the marker holder 16. For example, the second mold cavity is filled with liquid materials to form the lens body 14 and to bond the marker holder 16 with the top portion 24 of the lens body 14. While the second mold cavity is filled with the liquid materials of the lens body 14, the liquid materials flow into the metal receiver 40. The liquid materials of the lens body 14 fuse to the previously formed and partially cured marker holder 16.

The liquid materials of the lens body 14 fill empty space within the metal receiver 40 that is not occupied by the metal marker 12 as suggested in FIG. 4. The liquid materials of the lens body 14 filling the metal receiver 40 fixes the metal marker 12 in the metal receiver 40 such that removal of the metal marker 12 is prevented. For example, the back wall 44 of the marker holder 16 blocks rearward removal of the metal marker 12, and the top portion 24 of the lens body 14 blocks forward removal of the metal marker 12. Once the lens body 14 has cooled and hardened, the lens body 14 is removed from the second mold cavity.

Because the forwardly-facing metal receiver 40 is filled with the transparent liquid materials of the lens body 14, the metal marker 12 is visible from the front side of the protective eyewear 10 as shown in FIGS. 1 and 5. The metal marker 12 is visible to another person while the eyewear user is wearing the protective eyewear 10. In some embodiments, the metal marker 12 is not visible from other viewpoints (i.e., a top down view, a rear view, and/or a bottom up view) because of the marker holder 16. In other embodiments, the metal marker 12 is visible from other viewpoints.

No portions of the metal marker 12 are exposed to an external environment as the liquid materials of the lens body 14 closes the only opening into the metal receiver 40 as shown in FIG. 4. The filling of the metal receiver 40 with the liquid materials of the lens body 14 traps the metal marker 12 within the marker holder 16. The forwardly-facing metal receiver 40 opens only toward a portion of the lens body 14.

An additional component, such as a glue, that is different than the liquid materials of the marker holder 16 and the liquid materials of the lens body 14 is not needed to fill the metal receiver 40. The fusing of the lens body 14 with the marker holder 16 allows for a stronger bond between the two components, and thus, decreases the likelihood that the components will separate from one another.

In exemplary embodiments, the only metallic materials arranged between the first side 28 and the second side 30 of the lens body 14 is the metal marker 12 as shown in FIGS. 1 and 5. The metal marker 12 and/or other metallic components are not arranged along the bottom portion 26, the first side 28, or the second side 30 of the lens body 14.

The marker holder 16 advantageously provides increased durability to the protective eyewear 10. The marker holder 16 and the metal marker 12 arranged therein act as a stabilizing structure for the lens body 14 as the lens body 14 is formed on the marker holder 16. Additionally, the marker holder 16 allows for increased control over the optics of the lens body 14 as the lens body 14 is formed after the marker holder 16.

The protective eyewear 10 further comprises a first temple 48 and a second temple 50 as shown in FIGS. 1 and 2. The first temple 48 and the second temple 50 fit on respective ears of the eyewear user while the protective eyewear 10 is in use. The first temple 48 includes a first temple body 52 and a first temple plate 54 as shown in FIG. 13. The second temple 50 includes a second temple body 56 and a second temple plate 58 as shown in FIG. 14. The first temple body 52 is coupled with the first side 28 of the lens body 14 at the first hinge 32 for pivotable movement relative to the lens body 14. The second temple body 56 is coupled with the second side 30 of the lens body 14 at the second hinge 34 for pivotable movement relative to the lens body 14.

The first temple body 52 is formed to include a plate receiver 60 to receive the first temple plate 54 therein as shown in FIG. 13. The plate receiver 60 is illustratively formed as a recess in the first temple body 52. The first temple plate 54 comprises metallic materials such that the first temple 48 is metal detectable.

The first temple plate 54 is formed to include cutouts 62 and retainer receivers 66 extending through the first temple plate 54 as shown in FIG. 13. The cutouts 62 reduce a weight of the first temple plate 54. The first temple body 52 is formed to include protrusions 64 extending outwardly into the plate receiver 60 and configured to extend through the cutouts 62 of the first temple plate 54. The first temple body 52 is further formed to include retainers 68 extending outwardly into the plate receiver 60 to extend through the retainer receivers 66 of the first temple plate 54. The engagement of the retainers 68 and the retainer receivers 66 maintain a position of the first temple plate 54 in the plate receiver 60 after the first temple plate 54 is inserted into the plate receiver 60. As shown in FIG. 13, the first temple plate 54 extends throughout an entirety of the first temple body 52 to distribute the metallic materials throughout the first temple 48.

The second temple body 56 is formed to include a plate receiver 70 to receive the second temple plate 58 therein as shown in FIG. 14. The plate receiver 70 is illustratively formed as a recess in the second temple body 56. The second temple plate 58 comprises metallic materials such that the second temple 50 is metal detectable.

The second temple plate 58 is formed to include cutouts 72 and retainer receivers 74 extending through the second temple plate 58 as shown in FIG. 14. The cutouts 72 reduce a weight of the second temple plate 58. The second temple body 56 is formed to include protrusions 76 extending outwardly into the plate receiver 70 and configured to extend through the cutouts 72 of the second temple plate 58. The first temple body 52 is further formed to include retainers 78 extending outwardly into the plate receiver 70 to extend through the retainer receivers 74 of the second temple plate 58. The engagement of the retainers 78 and the retainer receivers 74 maintain a position of the second temple plate 58 in the plate receiver 70. As shown in FIG. 14, the second temple plate 58 extends throughout an entirety of the second temple body 56 to distribute the metallic materials throughout the second temple 50. In illustrative embodiments, the first temple plate 54 and the second temple plate 58 are formed of stainless steel.

To form the first temple 48, a third mold cavity is filled with liquid materials. The first temple 48 may be formed of polycarbonate or any other suitable material. A half piece of the first temple body 52 is formed to include the plate receiver 60 as shown in FIG. 13. The half piece of the first temple body 52 is illustratively formed through injection molding. The first temple plate 54 is inserted into the plate receiver 60 such that the retainers 68 of the first temple body 52 extend through the retainer receivers 66 of the first temple plate 54. The first temple plate 54 is arranged within the plate receiver 60 such that the protrusions 64 of the first temple body 52 extend through the cutouts 62 formed in the first temple plate 54. The retainers 68 maintain a fixed position of the first temple plate 54 within the plate receiver 60 until the first temple 48 is fully formed and hardened. In some embodiments, the first temple plate 54 is inserted into the plate receiver 60 by a technician. The third mold cavity is filled with additional liquid materials to form the remaining second half of the first temple body 52 such that the first temple plate 54 is entirely encased in the liquid materials of the first temple body 52 as shown in FIG. 1. The remaining second half of the first temple body 52 is illustratively formed through over molding.

To form the second temple 50, a fourth mold cavity is filled with liquid materials. The second temple 50 may be formed of polycarbonate or any other suitable material. A half piece of the second temple body 56 is formed to include the plate receiver 70. The half piece of the second temple body 56 is illustratively formed through injection molding. The second temple plate 58 is inserted into the plate receiver 70 such that the retainers 78 of the second temple body 56 extend through the retainer receivers 74 of the second temple plate 58. The second temple plate 58 is arranged within the plate receiver 70 such that the protrusions 76 of the second temple body 56 extend through the cutouts 72 formed in the second temple plate 58. The retainers 78 maintain a fixed position of the second temple plate 58 within the plate receiver 70 until the second temple 50 is fully formed and hardened. In some embodiments, the second temple plate 58 is inserted into the plate receiver 70 by a technician. The fourth mold cavity is filled with additional liquid materials to form the remaining second half of the second temple body 56 such that the second temple plate 58 is entirely encased in the liquid materials of the second temple body 56 as shown in FIG. 1. The remaining portion of the second temple body 56 is illustratively formed through over molding.

The first temple 48 is coupled with the lens body 14 at the first hinge 32 with a first hinge pin 80 as shown in FIGS. 1 and 2. The second temple 50 is coupled with the lens body 14 at the second hinge 34 with a second hinge pin 82 as shown in FIGS. 1 and 2. In illustrative embodiments, the first hinge pin 80 and the second hinge pin 82 are each formed of stainless steel such that the hinge pins 80, 82 are metal detectable. Illustratively, an air compressor presses the hinge pins 80, 82 into the first hinge 32 and the second hinge 34. The hinge pins 80, 82 are formed without threads.

The protective eyewear 10 includes a plurality of metal components comprising the metal marker 12, the first temple plate 54, the second temple plate 58, the first hinge pin 80, and the second hinge pin 82. The metal components provide metal detectability to each component of the protective eyewear 10, such as the first temple 48, the second temple 50, and the lens body 14. In some embodiments, the plurality of metal components weighs about 1.5 grams to about 2 grams. In some embodiments, the plurality of metal components weighs about 1.7 grams. For example, each of the first hinge pin 80 and the second hinge pin 82 weighs about 0.1 grams to about 0.2 grams. In some embodiments, each of the first hinge pin 80 and the second hinge pin 82 weighs about 0.15 grams. In some embodiments, each of the first hinge pin 80 and the second hinge pin 82 weighs about 0.16 grams. In some embodiments, each of the first temple plate 54 and the second temple plate 58 weighs about 0.4 grams to about 0.5 grams. In some embodiments, each of the first temple plate 54 and the second temple plate 58 weight about 0.45 grams. In some embodiments, each of the first temple plate 54 and the second temple plate 58 weighs about 0.44 grams. In some embodiments, the metal marker 12 weighs about 0.45 to about 0.55 grams. In some embodiments, the metal marker 12 weighs about 0.5 grams. In some embodiments, the metal marker 12 weighs about 0.49 grams.

In some embodiments, the protective eyewear 10 weighs about 26 grams to about 30 grams. In some embodiments, the protective eyewear 10 weighs about 28 grams. In some embodiments, at least about 25% to about 30% of the plurality of metal components are positioned to lie above the lens body 14. In some embodiments, at least about 28% to about 30% of the plurality of metal components are positioned to lie above the lens body 14. In some embodiments, at least about 29% of the plurality of metal components are positioned to lie above the lens body 14.

A method 110 of making the protective eyewear 10 is provided herein and shown in FIG. 3. The method 110 includes a step of filling 120 the first mold cavity with liquid materials. The method 110 includes a step of forming 130 the marker holder 16 to include the metal receiver 40. The method 110 includes a step of inserting 140 the metal marker 12 into the marker holder 16 through the forwardly-facing opening of the marker holder 16. The method 110 includes a step of inserting 150 the marker holder 16 with the metal marker 12 therein into the second mold cavity. The method 110 includes a step of filling 160 the second mold cavity with liquid materials. The method 110 includes a step of forming 170 the lens body 14 fused with the marker holder 16. The method 110 includes a step of forming 180 the first temple 48. The method 110 includes a step of forming 190 the second temple 50. The method 110 includes a step of coupling 200 the first temple 48 and the second temple 50 to the lens body 14 with the hinge pins 80, 82. The method may include applying a coating on the lens body 14, such as an antifog and/or an abrasion treatment.

The invention claimed is:

1. Protective eyewear comprising:

a lens body configured to protect eyes of a user, the lens body having a first lens, a second lens, and a nosepiece interconnecting the first lens and the second lens, a metal marker including metallic materials, and a marker holder formed to include a forwardly-facing metal receiver to receive the metal marker therein and configured to couple the metal marker to the lens body without embedding the metal marker in the lens body, wherein the marker holder is coupled to a top portion of the lens body to extend above the first lens, the second lens, and the nosepiece, wherein the forwardly-facing metal receiver formed in the marker holder is a long, narrow groove that extends above the first lens, the second lens, and the nosepiece and is sized to receive the metal marker therein, and the long, narrow groove formed in the marker holder is filled with materials of the lens body to prevent removal of the metal marker therefrom.

2. The protective eyewear of claim 1, wherein the marker holder forms a topmost portion of the protective eyewear.

3. The protective eyewear of claim 1, wherein the forwardly-facing metal receiver opens only toward a portion of the lens body.

4. The protective eyewear of claim 1, wherein the metal marker is an elongated metal wire having a uniform cylindrical cross-sectional shape.

5. The protective eyewear of claim 4, wherein the lens body has a first top length, the long, narrow groove formed in the marker holder has a second top length, and the metal marker has a third top length, the first top length is greater than the second top length, and the second top length is greater than the third top length.

6. The protective eyewear of claim 4, wherein the metal marker is formed as a single, integral component.

7. The protective eyewear of claim 1, wherein the protective eyewear comprises a plurality of metal components including the metal marker, a first hinge pin, a second hinge pin, a first temple plate, and a second temple plate, and wherein at least about 29% of the plurality of metal components are positioned to lie above the lens body.

8. The protective eyewear of claim 1, further comprising a first temple coupled to the lens body and configured to support the lens body relative to the user upon placement of the protective eyewear on the user, the first temple including a first temple body formed to include a first plate receiver and a first temple plate comprising metallic materials and configured to lie in the first plate receiver of the first temple body, and wherein the first temple plate is formed to include a retainer receiver extending through the first temple plate, and wherein the first temple body is formed to include a retainer extending outwardly into the plate receiver to extend through the retainer receiver of the first temple plate to maintain a position of the first temple plate in the first plate receiver.

9. Protective eyewear comprising:

a lens body having a first lens, a second lens, and a nosepiece interconnecting the first lens and the second lens, a metal marker including metallic materials, and a marker holder configured to couple the metal marker to the lens body without embedding the metal marker in the lens body, the marker holder formed to include a metal receiver to receive the metal marker therein, and the marker holder being coupled to a top portion of the lens body to extend above the first lens, the second lens, and the nosepiece, wherein the metal receiver formed in the marker holder is a forwardly-facing groove sized to receive the metal marker therein, and the forwardly-facing groove extends above the first lens, the second lens, and the nosepiece, wherein the forwardly-facing groove is filled with materials of the lens body to prevent removal of the metal marker therefrom.

10. The protective eyewear of claim 9, wherein the metal marker is an elongated metal wire having a uniform cylindrical cross-sectional shape and the metal marker extends above the first lens, the second lens, and the nosepiece.

11. The protective eyewear of claim 9, wherein the protective eyewear comprises a plurality of metal components including the metal marker, a first hinge pin, a second hinge pin, a first temple plate, and a second temple plate, and wherein at least about 29% of the plurality of metal components are positioned to lie above the lens body.

12. A method of making protective eyewear comprising:

providing a first mold cavity, a second mold cavity, and a metal marker, filling the first mold cavity with a first liquid material to form a marker holder including an elongated forwardly-facing groove, inserting the metal marker comprising an elongated metal wire into the elongated forwardly-facing groove, inserting the marker holder with the metal marker positioned therein into the second mold cavity, filling the second mold cavity with a second liquid material, and forming a lens body coupled with the marker holder, the lens body being configured to protect eyes of a user and the lens body having a first lens, a second lens, and a nosepiece interconnecting the first lens and the second lens, wherein the step of forming includes filling the elongated forwardly-facing groove with the second liquid material of the lens body so that the elongated metal wire is fixed in the elongated forwardly-facing groove.

13. The method of claim 12, wherein the step of forming includes fusing the marker holder to a top portion of the lens body.

14. The method of claim 12, further comprising bending the metal marker to match a shape of the elongated forwardly-facing groove.

* * * * *